United States Patent
Kawata et al.

(10) Patent No.: US 6,424,151 B2
(45) Date of Patent: Jul. 23, 2002

(54) METHOD AND APPARATUS FOR EVALUATION OF EDDY CURRENT TESTING SIGNAL

(75) Inventors: Kayoko Kawata; Masaaki Kurokawa, both of Takasago; Yoshihiro Asada, Kobe, all of (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 2 days.

(21) Appl. No.: 09/756,139

(22) Filed: Jan. 9, 2001

(30) Foreign Application Priority Data

Jul. 6, 2000 (JP) .......................... 2000-204665

(51) Int. Cl.$^7$ .......................... G01N 27/90; G06F 15/18
(52) U.S. Cl. .................. 324/233; 324/220; 324/240; 702/38
(58) Field of Search ................ 324/229, 233, 324/238, 239, 234, 236, 237, 240, 241, 242, 243, 219, 220; 702/38, 39

(56) References Cited

U.S. PATENT DOCUMENTS

| | | | |
|---|---|---|---|
| 4,213,183 A | * | 7/1980 | Barron et al. .................. 702/39 |
| 4,954,778 A | * | 9/1990 | Champonnois et al. ...... 324/233 |
| 5,339,256 A | * | 8/1994 | Levy et al. .................... 702/38 |
| 5,737,445 A | * | 4/1998 | Oppenlander et al. ....... 382/207 |
| 6,115,674 A | * | 9/2000 | Brudnoy et al. .............. 702/38 |

FOREIGN PATENT DOCUMENTS

JP 11002626 A * 1/1999 .......... G01N/27/90

OTHER PUBLICATIONS

Sikora et al., "Artificial Neural Network Application for material evaluation by electromagnetic methods", International Joint Conference on Neural Networks, 1999, vol. 6, pp. 4027–4032.*

* cited by examiner

*Primary Examiner*—Edward Lefkowitz
*Assistant Examiner*—Darrell Kinder

(57) ABSTRACT

A method for evaluation of an eddy current testing signal is provided. The method includes the steps of generating a feature amount based on a sample eddy current testing signal obtained by measuring a standard specimen, the feature amount including a feature highly correlated to a secondary factor which is other than a depth of the flaw and which affects the waveform of the signal; generating an evaluation parameter by using the feature amount, the evaluation parameter being a parameter for outputting a value with a sufficiently small error relative to correct answer data on the sample eddy current testing signal; and estimating the depth of a flaw, expressed by an actual measurement eddy current testing signal, by use of the evaluation parameter.

16 Claims, 8 Drawing Sheets

METHOD AND APPARATUS FOR EVALUATION OF EDDY CURRENT TESTING SIGNAL

BACKGROUND OF THE INVENTION

1. Field of the Invention

The present invention relates to a method and an apparatus for evaluation of an eddy current testing (or ECT) signal. More specifically, the invention relates to the method and apparatus useful when applied to flaw detection using an eddy current testing sensor on a multi-coil system, a rotation system, or a two-dimensional scanning system (hereinafter referred to as the multi-coil system or the like).

2. Description of Related Art

Eddy current testing is known as a method for nondestructive testing of a metal. This method involves generating an eddy current in a member to be measured, by a magnetic flux generated by a coil supplied with an exciting current, and obtaining an eddy current testing signal based on a magnetic flux generated by the eddy current as an output signal from the coil. The eddy current testing signal reflects the location, shape, depth, etc. of a flaw existing in the member to be measured. Based on this eddy current testing signal, the member to be measured, which is a metal (magnetic material), can be inspected nondestructively.

To test, for example, a heat exchange tube for a flaw by the eddy current testing method, a coil, which is an eddy current testing sensor, is inserted into the heat exchange tube to obtain an eddy current testing signal. Such a signal representing a flaw changes not only in amplitude, but also in phase. Thus, observation of the eddy current testing signal in one-dimension is not sufficient, and its two-dimensional observation is necessary. Hence, the eddy current testing of the heat exchange tube uses an eddy current testing apparatus which generates a two-dimensional output appearing along an X-axis and a Y-axis. An eddy current testing signal expressed on a voltage plane draws a Lissajous' figure as shown in FIG. 7.

Such a Lissajous' figure is characterized by its size and its slope relative to the X-axis. That is, the size of the Lissajous' figure is proportional to the volume of the flaw, and its slope relative to the X-axis corresponds to the depth of the flaw. In the eddy current testing of a heat exchange tube, the depth of the flaw is important information. Thus, flaw detection is performed in a predetermined manner based on the phase of the eddy current testing signal. In detail, the phase angle of the eddy current testing signal (a value as a complex number) representing a flaw is measured. The measured phase angle is mapped on a characteristic curve (prepared beforehand) as shown in FIG. 8 which illustrates the relationship between the phase angle of an eddy current testing signal and the depth of a flaw. Based on a reading taken from the characteristic curve, the depth of the flaw is estimated.

As described above, eddy current testing according to the earlier technologies measures the phase angle of the eddy current testing signal, and maps the measured value on the prepared characteristic curve illustrating the relationship between the phase angle of the eddy current testing signal and the depth of the flaw to estimate the depth of the flaw. However, the phase angle and the depth of the flaw do not necessarily correlate exactly, and the accuracy of flaw detection may be practically insufficient. This is because, given the same depth of the flaw, the phase angle may vary according to various factors, such as the shape of the flaw (e.g., length, width) and the relative positional relationship between the flaw and the coil. Particularly in the case of an internal flaw (a flaw on an inner peripheral surface of a heat exchange tube) showing a low rate of change in the depth of flaw in comparison with the rate of change in the phase angle of the eddy current testing signal, the accuracy of flaw detection may often be problematical.

SUMMARY OF THE INVENTION

The present invention has been accomplished in light of the problems with earlier technologies. An object of the invention is to provide a method and an apparatus for evaluation of an eddy current testing signal, the method and apparatus being capable of improving accuracy in evaluating the depth of a flaw detected by eddy current testing, and increasing accuracy in evaluating the amount of a decrease in the wall thickness of a member to be measured, as well as accuracy in discerning a false signal.

To attain the above object, the invention is characterized by the following aspects:

1) A method for generating a feature amount from an eddy current testing signal, comprising:

generating the feature amount based on the eddy current testing signal obtained by measuring a member to be measured, the feature amount being a numerical expression of not only a phase angle of the eddy current testing signal highly correlated to a depth of a flaw, and an amplitude of the eddy current testing signal, but also a feature highly correlated to a secondary factor which is other than the depth of the flaw and which affects a waveform of the eddy current testing signal.

According to this aspect, signals around a peak of the eddy current testing signal can be incorporated into the feature amount. This makes it possible to quantify an influence which elements affecting the evaluation of an eddy current testing signal, i.e., elements becoming the cause of a noise when the depth of a flaw is evaluated by use of the phase angle and the amplitude alone, exert on the evaluation of the flaw depth. Consequently, this aspect of the invention can provide data for more accurate determination of the depth of a flaw on the basis of an eddy current testing signal.

2) A method for evaluation of an eddy current testing signal, comprising:

generating a feature amount based on a sample eddy current testing signal obtained by measuring a standard specimen as a member to be measured and of a known depth of a flaw, the feature amount being a numerical expression of not only a phase angle of the sample eddy current testing signal highly correlated to the depth of the flaw, and an amplitude of the sample eddy current testing signal, but also a feature highly correlated to a secondary factor which is other than the depth of the flaw and which affects a waveform of the sample eddy current testing signal;

generating an evaluation parameter by learning with use of the feature amount, the evaluation parameter being a parameter for outputting a value with a sufficiently small error relative to known correct answer data as an amount expressing the depth of the flaw of the standard specimen;

generating a feature amount similar to that from the sample eddy current testing signal by use of an actual measurement eddy current testing signal obtained by eddy current testing of a member as an object to be measured; and generating data representing the depth of the flaw on the basis of the feature amount based on the actual measurement eddy current testing signal, and the evaluation parameter corresponding to the feature amount.

According to this aspect, a feature amount as a numerical expression of features effective for evaluation of the depth of a flaw is statistically processed to generate a single evaluation parameter. The use of such a single evaluation parameter enables the depth of the flaw to be evaluated based on an actual measurement eddy current testing signal. Consequently, this aspect of the invention can markedly improve accuracy of evaluation in comparison with a judgment of the depth of the flaw based only on the phase angle and amplitude of the actual measurement eddy current testing signal.

3) The method for evaluation of an eddy current testing signal as described in 2), comprising:

classifying a type of the flaw, such as an external flaw or an internal flaw, based on the sample eddy current testing signal, and generating a similar feature amount and a similar evaluation parameter according to the classified type; and classifying a type of the flaw based on the actual measurement eddy current testing signal obtained by eddy current testing of the member to be measured, and performing generation of a feature amount according to the classified type, and generation of data representing the depth of the flaw based on the evaluation parameter according to the classified type.

According to this aspect, the method for evaluation described in 2) can be performed according to the type of a flaw. Consequently, this aspect of the invention can evaluate the depth of the flaw more accurately than the aspect of invention 2).

4) A method for evaluation of an eddy current testing signal, comprising:

generating feature amounts based on a plurality of sample eddy current testing signals obtained by measuring a standard specimen, as a member to be measured and with a known amount of decrease in wall thickness, by means of an eddy current testing sensor for obtaining data at many locations distributed in two-dimensions, such as a multi-coil system sensor having many coils, the feature amounts being numerical expressions of not only phase angles of the sample eddy current testing signals highly correlated to the amount of decrease in wall thickness, and amplitudes of the sample eddy current testing signals, but also a feature highly correlated to a secondary factor which is other than the amount of decrease in wall thickness and which affects waveforms of the sample eddy current testing signals;

sorting the feature amounts based on the sample eddy current testing signals according to predetermined standards, such as a sequence of phase, so that an efficiency of subsequent learning is improved;

generating an evaluation parameter by learning with use of the feature amounts, the evaluation parameter being a parameter for outputting a value with a sufficiently small error relative to known correct answer data as an amount expressing the amount of decrease in the wall thickness of the standard specimen;

generating feature amounts similar to those from the sample eddy current testing signals by use of actual measurement eddy current testing signals obtained by eddy current testing of a member to be measured; and generating data representing the amount of decrease in the wall thickness on the basis of the feature amounts based on the actual measurement eddy current testing signals, and the evaluation parameter corresponding to the feature amounts.

According to this aspect, feature amounts as numerical expressions of features effective for evaluation of the amount of decrease in wall thickness are statistically processed to generate a single evaluation parameter. The use of such an evaluation parameter enables the amount of decrease in wall thickness to be evaluated based on actual measurement eddy current testing signals. Consequently, this aspect of the invention can markedly improve accuracy of evaluation in comparison with a judgment of the amount of decrease in wall thickness based only on the phase angles and amplitudes of the actual measurement eddy current testing signals.

5) A method for evaluation of an eddy current testing signal, comprising:

generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal highly correlated to a flaw, and an amplitude of the sample eddy current testing signal, but also a feature highly correlated to a secondary factor which affects a waveform of the sample eddy current testing signal;

generating an evaluation parameter by learning with use of the feature amount, the evaluation parameter being a parameter for outputting a value with a sufficiently small error relative to known correct answer data as a state signal representing the flaw or pseudo-factor of the standard specimen;

generating a feature amount similar to that from the sample eddy current testing signal by use of an actual measurement eddy current testing signal obtained by eddy current testing of a member to be measured; and generating a state signal representing the flaw or the pseudo-factor on the basis of the feature amount based on the actual measurement eddy current testing signal, and the evaluation parameter corresponding to the feature amount.

According to this aspect, a feature amount as a numerical expression of features effective for evaluating whether the state under evaluation is a flaw or other pseudo-factor is statistically processed to generate a single evaluation parameter. The use of such an evaluation parameter makes it possible to evaluate whether the state under evaluation is a flaw or other pseudo-factor. Consequently, this aspect of the invention can markedly improve accuracy of evaluation in comparison with judging, based only on the phase angle and amplitude, whether the state under evaluation is a flaw or other pseudo-factor.

6) An apparatus for evaluation of an eddy current testing signal, comprising:

feature amount generation means for receiving a sample eddy current testing signal obtained by measuring a standard specimen as a member to be measured and of a known depth of a flaw, and generating a feature amount being a numerical expression of not only a phase angle of the sample eddy current testing signal highly correlated to the depth of the flaw, and an amplitude of the sample eddy current testing signal, but also a feature highly correlated to a secondary factor which is other than the depth of the flaw and which affects a waveform of the sample eddy current testing signal;

correct answer data supply means for supplying known correct answer data as an amount expressing the depth of the flaw of the standard specimen;

learning means for receiving the feature amount and the correct answer data, and generating an evaluation parameter by learning with use of the feature amount, the evaluation parameter being a parameter for outputting a value with a sufficiently small error relative to the correct answer data;

feature amount generation means for generating a feature amount similar to that from the sample eddy current testing signal by use of an actual measurement eddy current testing signal obtained by eddy current testing of a member as an object to be measured; and evaluation results generation means for generating data representing the depth of the flaw on the basis of the feature amount based on the actual measurement eddy current testing signal, and the evaluation parameter corresponding to the feature amount.

According to this aspect, a feature amount as a numerical expression of features effective for evaluation of the depth of the flaw is statistically processed to generate a single evaluation parameter. The use of such an evaluation parameter enables the depth of the flaw to be evaluated based on an actual measurement eddy current testing signal. Consequently, this aspect of the invention can markedly improve accuracy of evaluation in comparison with a judgment of the depth of the flaw based only on the phase angle and amplitude of the actual measurement eddy current testing signal.

It is difficult for a person to evaluate the depth of a flaw with the use of a feature element other than a phase angle. According to the above aspect, on the other hand, various feature elements other than a phase angle are statistically processed to generate an evaluation parameter. Hence, an eddy current testing signal can be judged globally, so that the accuracy of evaluation can be improved.

7) The apparatus for evaluation of an eddy current testing signal as described in 6), including:

classification means for classifying a type of flaw, such as an external flaw or an internal flaw, based on the actual measurement eddy current testing signal obtained by eddy current testing of the member to be measured;

evaluation parameter generation means adapted to classify the type of the flaw based on the sample eddy current testing signal, and generate the feature amount and the evaluation parameter according to the classified type;

the feature amount generation means for generating the feature amount based on the actual measurement eddy current testing signal being adapted to generate the feature amount according to a classification made by the classification means; and the evaluation results generation means being adapted to generate the data representing the depth of the flaw on the basis of the feature amount and the evaluation parameter generated according to the classification.

According to this aspect, the method for evaluation described in 6) can be performed according to the type of a flaw. Consequently, this aspect of the invention can evaluate the depth of the flaw more accurately than the aspect of invention 6).

8) An apparatus for evaluation of an eddy current testing signal, comprising:

feature amount generation means for generating feature amounts based on a plurality of sample eddy current testing signals obtained by measuring a standard specimen, as a member to be measured and with a known amount of decrease in wall thickness, by means of an eddy current testing sensor for obtaining data at many locations distributed in two-dimensions, such as a multi-coil system sensor having many coils, the feature amounts being numerical expressions of not only phase angles of the sample eddy current testing signals highly correlated to the amount of decrease in wall thickness, and amplitudes of the sample eddy current testing signals, but also a feature highly correlated to a secondary factor which is other than the amount of decrease in wall thickness and which affects waveforms of the sample eddy current testing signals;

sorting means for sorting the feature amounts based on the sample eddy current testing signals according to predetermined standards, such as a sequence of phase, so that an efficiency of subsequent learning is improved;

correct data supply means for supplying known correct answer data as an amount expressing the amount of decrease in the wall thickness of the standard specimen;

learning means for receiving the feature amounts and the correct answer data, and generating an evaluation parameter by learning with use of the feature amounts, the evaluation parameter being a parameter for outputting a value with a sufficiently small error relative to the correct answer data;

feature amount generation means for generating feature amounts similar to those from the sample eddy current testing signals by use of actual measurement eddy current testing signals obtained by eddy current testing of a member as an object to be measured; and evaluation results generation means for generating data representing an amount of decrease in the wall thickness on the basis of the feature amounts based on the actual measurement eddy current testing signals, and the evaluation parameter corresponding to the feature amounts.

According to this aspect, feature amounts as numerical expressions of features effective for evaluating the amount of decrease in wall thickness are statistically processed to generate a single evaluation parameter. The use of such an evaluation parameter enables the amount of decrease in wall thickness to be evaluated based on actual measurement eddy current testing signals. Consequently, this aspect of the invention can markedly improve accuracy of evaluation in comparison with a judgment of the amount of decrease in wall thickness based only on the phase angles and amplitudes of the actual measurement eddy current testing signals.

It is difficult for a person to evaluate the amount of decrease in wall thickness with the use of a feature element other than a phase angle. According to this aspect of the invention, on the other hand, various feature elements other than a phase angle are statistically processed to generate an evaluation parameter. Hence, an eddy current testing signal can be judged globally, so that the accuracy of evaluation can be improved.

9) An apparatus for evaluation of an eddy current testing signal, comprising:

feature amount generation means for generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal highly correlated to a flaw, and an amplitude of the sample eddy current testing signal, but also a feature highly correlated to a secondary factor which affects a waveform of the sample eddy current testing signal;

correct data supply means for supplying known correct answer data as a state signal generated responsive to and expressing the flaw or pseudo-factor of the standard specimen;

learning means for receiving the feature amount and the correct answer data, and generating an evaluation parameter by learning with use of the feature amount, the evaluation parameter being a parameter for outputting a value with a sufficiently small error relative to the correct answer data;

feature amount generation means for generating a feature amount similar to that from the sample eddy current testing signal by use of an actual measurement eddy current testing signal obtained by eddy current testing of a member as an object to be measured; and evaluation results generation means for generating a state signal representing a flaw or a pseudo-factor on the basis of the feature amount based on the actual measurement eddy current testing signal, and the evaluation parameter corresponding to the feature amount.

According to this aspect, a feature amount as a numerical expression of features effective for evaluating whether the state under evaluation is a flaw or other pseudo-factor is statistically processed to generate a single evaluation parameter. The use of such an evaluation parameter, makes it possible to evaluate whether the state under evaluation is a flaw or other pseudo-factor. Consequently, this aspect of the invention can markedly improve accuracy of evaluation in comparison with judging, based only on the phase angle and amplitude, whether the state under evaluation is a flaw or other pseudo-factor.

It is difficult for a person to evaluate, with the use of a feature element other than a phase angle, whether the state under evaluation is a flaw or other pseudo-factor. According to the above aspect of the invention, on the other hand, various feature elements other than a phase angle are statistically processed to generate an evaluation parameter. Hence, an eddy current testing signal can be judged globally, so that the accuracy of evaluation can be improved.

10) A method for evaluation of an eddy current testing signal, comprising:

generating a feature amount based on a sample eddy current testing signal obtained by measuring a standard specimen as a member to be measured and of a known depth of a flaw, the feature amount being a numerical expression of not only a phase angle of the sample eddy current testing signal highly correlated to the depth of the flaw, and an amplitude of the sample eddy current testing signal, but also a feature highly correlated to a secondary factor which is other than the depth of the flaw and which affects a waveform of the sample eddy current testing signal;

generating an evaluation parameter by learning with use of the feature amount, the evaluation parameter being a parameter for leading to known correct answer data as an amount expressing the depth of the flaw of the standard specimen;

repeating operations for generation of the feature amount based on the sample eddy current testing signal and generation of the evaluation parameter, with a combination of elements of the feature amount being changed, to generate a plurality of evaluation parameters;

generating a plurality of feature amounts similar to those from the sample eddy current testing signals for different combinations of elements of the feature amount by use of actual measurement eddy current testing signals obtained by eddy current testing of a member as an object to be measured;

generating data representing the depths of the flaw for the respective evaluation parameters on the basis of the respective feature amounts based on the actual measurement eddy current testing signals, and the respective evaluation parameters corresponding to the respective feature amounts; and comparing the respective data representing the depths of the flaw, and when the depths of the flaw represented by the respective data fall within a predetermined range, adopting the depth of the flaw based on the predetermined range as an estimated value.

According to this aspect, a plurality of feature amounts as numerical expressions of features effective for evaluation of the depth of the flaw are statistically processed to generate a plurality of evaluation parameters. The use of such evaluation parameters enables the depth of the flaw to be evaluated based on an actual measurement eddy current testing signal. Consequently, this aspect of the invention can markedly improve accuracy of evaluation in comparison with a judgment of the depth of the flaw based only on the phase angle and amplitude of the actual measurement eddy current testing signal. Since the plural feature amounts and evaluation parameters are used, moreover, more accurate evaluation than with the use of a single feature amount and a single evaluation parameter can be made.

11) The method for evaluation of an eddy current testing signal as described in 10), comprising:

classifying a type of the flaw, such as an external flaw or an internal flaw, based on the sample eddy current testing signal, and performing similar generation of feature amounts and evaluation parameters according to the classified type; and classifying a type of the flaw based on the actual measurement eddy current testing signal obtained by eddy current testing of the member to be measured, and performing generation of the feature amounts according to the classified type and generation of the data representing the depth of the flaw based on the feature amounts and evaluation parameters according to the classified type.

According to this aspect, the method for evaluation described in 10) can be performed according to the type of a flaw. Consequently, this aspect of the invention can evaluate the depth of the flaw more accurately than the aspect of invention 10). Since the plurality of feature amounts and evaluation parameters are used, moreover, it is possible to make more accurate evaluation than with the use of a single feature amount and a single evaluation parameter.

12) A method for evaluation of an eddy current testing signal, comprising:

generating feature amounts based on a plurality of sample eddy current testing signals obtained by measuring a standard specimen, as a member to be measured and with a known amount of decrease in wall thickness, by means of an eddy current testing sensor for obtaining data at many locations distributed in two-dimensions, such as a multi-coil system sensor having many coils, the feature amounts being numerical expressions of not only phase angles of the sample eddy current testing signals highly correlated to the amount of decrease in wall thickness, and amplitudes of the sample eddy current testing signals, but also a feature highly correlated to a secondary factor which is other than the amount of decrease in wall thickness and which affects waveforms of the sample eddy current testing signals;

sorting the feature amounts based on the sample eddy current testing signals according to predetermined standards, such as a sequence of phase, so that an efficiency of subsequent learning is improved;

generating an evaluation parameter by learning with use of the feature amounts, the evaluation parameter being a parameter for outputting a value with a sufficiently small error relative to known correct answer data as an amount expressing the amount of decrease in the wall thickness of the standard specimen;

repeating operations for generation of the feature amounts based on the sample eddy current testing signals, sorting, and generation of the evaluation parameter, while changing a combination of elements of the feature amount and the standards for sorting, to generate a plurality of evaluation parameters;

generating a plurality of feature amounts similar to those from the sample eddy current testing signals for different combinations of elements of the feature amount by use of actual measurement eddy current testing signals obtained by eddy current testing of a member as an object to be measured;

generating data representing the amounts of decrease in the wall thickness for the respective evaluation parameters on the basis of the respective feature amounts based on the actual measurement eddy current testing signals, and the respective evaluation parameters corresponding to the respective feature amounts; and comparing the respective data representing the amounts of decrease in the wall thickness, and when the amounts of decrease in the wall thickness represented by the respective data fall within a predetermined range, adopting the amount of decrease in the wall thickness based on the predetermined range as an estimated value.

According to this aspect, a plurality of feature amounts as numerical expressions of features effective for evaluating the amount of decrease in wall thickness are statistically processed to generate a plurality of evaluation parameters. The use of such evaluation parameters enables the amount of decrease in wall thickness to be evaluated based on actual measurement eddy current testing signals. Consequently, this aspect of the invention can markedly improve accuracy of evaluation in comparison with a judgment of the amount of decrease in wall thickness based only on the phase angles and amplitudes of the actual measurement eddy current testing signals. Since the plural feature amounts and evaluation parameters are used, moreover, more accurate evaluation than by use of a single feature amount and a single evaluation parameter can be made.

13) A method for evaluation of an eddy current testing signal, comprising:

generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal highly correlated to a flaw, and an amplitude of the sample eddy current testing signal, but also a feature highly correlated to a secondary factor which affects a waveform of the sample eddy current testing signal;

generating an evaluation parameter by learning with use of the feature amount, the evaluation parameter being a parameter for outputting a value with a sufficiently small error relative to known correct answer data as a state signal representing the flaw or pseudo-factor of the standard specimen;

repeating operations for generation of the feature amount based on the sample eddy current testing signal, and generation of the evaluation parameter, while changing a combination of elements of the feature amount, to generate a plurality of evaluation parameters;

generating a plurality of feature amounts similar to those from the sample eddy current testing signal for different combinations of elements of the feature amount by use of an actual measurement eddy current testing signal obtained by eddy current testing of a member to be measured;

generating state signals representing a flaw or a pseudo-factor for the respective evaluation parameters on the basis of the respective feature amounts based on the actual measurement eddy current testing signal, and the respective evaluation parameters corresponding to the respective feature amounts; and comparing the respective state signals to discern, based on coincidence of contents of the state signals, whether the actual measurement eddy current testing signal is a signal representing a flaw, or a false signal.

According to this aspect, plural feature amounts as numerical expressions of features effective for evaluating whether the state under evaluation is a flaw or other pseudo-factor are statistically processed to generate plural evaluation parameters. The use of such evaluation parameters makes it possible to evaluate whether the state under evaluation is a flaw or other pseudo-factor. Consequently, this aspect of the invention can markedly improve accuracy of evaluation in comparison with judging, based only on the phase angle and amplitude, whether the state under evaluation is a flaw or other pseudo-factor. Since the plural feature amounts and evaluation parameters are used, moreover, more accurate evaluation than when using a single feature amount and a single evaluation parameter can be made.

14) An apparatus for evaluation of an eddy current testing signal, comprising:

feature amount generation means for receiving a sample eddy current testing signal obtained by measuring a standard specimen as a member to be measured and of a known depth of a flaw, and generating a feature amount being a numerical expression of not only a phase angle of the sample eddy current testing signal highly correlated to the depth of the flaw, and an amplitude of the sample eddy current testing signal, but also a feature highly correlated to a secondary factor which is other than the depth of the flaw and which affects a waveform of the sample eddy current testing signal:

correct answer data supply means for supplying known correct answer data as an amount expressing the depth of the flaw of the standard specimen;

learning means for receiving the feature amount and the correct answer data, and generating an evaluation parameter by learning with use of the feature amount, the evaluation parameter being a parameter for outputting a value with a sufficiently small error relative to the correct answer data;

evaluation parameter generation means for repeating operations for generation of the feature amount based on the sample eddy current testing signal and generation of the evaluation parameter, with a combination of elements of the feature amount being changed, to generate a plurality of evaluation parameters;

feature amount generation means for generating a plurality of feature amounts similar to those from the sample eddy current testing signal for different combinations of elements of the feature amount by use of an actual measurement eddy current testing signal obtained by eddy current testing of a member as an object to be measured;

evaluation results generation means for generating data representing depths of a flaw for the respective evaluation parameters on the basis of the respective feature amounts based on the actual measurement eddy current testing signal, and the respective evaluation parameters corresponding to the respective feature amounts; and verification means for comparing the respective data representing the depths of the flaw which have been obtained as output signals from the evaluation results generation means, and when the depths of the flaw represented by the respective data fall within a predetermined range, adopting the depth of the flaw based on the predetermined range as an estimated value.

According to this aspect, plural feature amounts as numerical expressions of features effective for evaluation of the depth of the flaw are statistically processed to generate plural evaluation parameters. The use of such evaluation parameters enables the depth of the flaw to be evaluated based on an actual measurement eddy current testing signal. Consequently, this aspect of the invention can markedly improve accuracy of evaluation in comparison with a judgment of the depth of the flaw based only on the phase angle and amplitude of the actual measurement eddy current testing signal.

It is difficult for a person to evaluate the depth of a flaw with the concomitant use of a feature element other than a phase angle. According to this aspect of the invention, on the other hand, various feature elements other than a phase angle are statistically processed to generate an evaluation parameter. Hence, an eddy current testing signal can be judged globally, so that the accuracy of evaluation can be improved. Since the plural feature amounts and evaluation parameters are used, moreover, more accurate evaluation than when using a single feature amount and a single evaluation parameter can be made.

15) The apparatus for evaluation of an eddy current testing signal as described in 14), including:

classification means for classifying a type of flaw, such as an external flaw or an internal flaw, based on the actual measurement eddy current testing signal obtained by eddy current testing of the member to be measured;

the evaluation parameter generation means being adapted to classify the type of the flaw based on the sample eddy current testing signal, and generate the feature amount and the evaluation parameter according to the classified type;

the feature amount generation means for generating the feature amount based on the actual measurement eddy current testing signal being adapted to generate the feature amount according to a classification made by the classification means; and the evaluation results generation means being adapted to generate the data representing the depth of the flaw on the basis of the feature amount and the evaluation parameter generated according to the classification.

According to this aspect, the method for evaluation described in 14) can be performed according to the type of a flaw. Consequently, this aspect of the invention can evaluate the depth of the flaw more accurately than the aspect of invention 14). Since the plural feature amounts and evaluation parameters are used, moreover, more accurate evaluation than with the use of a single feature amount and a single evaluation parameter can be made.

16) An apparatus for evaluation of an eddy current testing signal, comprising:

feature amount generation means for generating feature amounts based on a plurality of sample eddy current testing signals obtained by measuring a standard specimen, as a member to be measured and with a known amount of decrease in wall thickness, by means of an eddy current testing sensor for obtaining data at many locations distributed in two-dimensions, such as a multi-coil system sensor having many coils, the feature amounts being numerical expressions of not only phase angles of the sample eddy current testing signals highly correlated to the amount of decrease in wall thickness, and amplitudes of the sample eddy current testing signals, but also a feature highly correlated to a secondary factor which is other than the amount of decrease in wall thickness and which affects waveforms of the sample eddy current testing signals;

sorting means for sorting the feature amounts based on the sample eddy current testing signals according to predetermined standards, such as a sequence of phase, so that an efficiency of subsequent learning is improved;

correct data supply means for supplying known correct answer data as an amount expressing the amount of decrease in the wall thickness of the standard specimen;

learning means for receiving the feature amounts and the correct answer data, and generating an evaluation parameter by learning with use of the feature amounts, the evaluation parameter being a parameter for outputting a value with a sufficiently small error relative to the correct answer data;

evaluation parameter generation means for repeating operations for generation of the feature amounts based on the sample eddy current testing signals, sorting, and generation of the evaluation parameter, while changing a combination of elements of the feature amount and the standards for sorting, to generate a plurality of evaluation parameters;

feature amount generation means for generating a plurality of feature amounts similar to those from the sample eddy current testing signals for different combinations of elements of the feature amount by use of actual measurement eddy current testing signals obtained by eddy current testing of a member as an object to be measured;

evaluation results generation means for generating data representing the amounts of decrease in the wall thickness for the respective evaluation parameters on the basis of the respective feature amounts based on the actual measurement eddy current testing signals, and the respective evaluation parameters corresponding to the respective feature amounts; and verification means for comparing the respective data representing the amounts of decrease in the wall thickness which have been obtained as output signals from the evaluation results generation means, and when the amounts of decrease in the wall thickness represented by the respective data fall within a predetermined range, adopting the amount of decrease in the wall thickness based on the predetermined range as an estimated value.

According to this aspect, plural feature amounts as numerical expressions of features effective for evaluating the amount of decrease in wall thickness are statistically processed to generate plural evaluation parameters. The use of such evaluation parameters enables the amount of decrease in wall thickness to be evaluated based on actual measurement eddy current testing signals. Consequently, this aspect of the invention can markedly improve accuracy of evaluation in comparison with a judgment of the amount of decrease in wall thickness based only on the phase angles and amplitudes of the actual measurement eddy current testing signals.

In making evaluation, a person finds difficulty in evaluating the amount of decrease in wall thickness with the concomitant use of a feature element other than a phase angle. According to the above aspect of the invention, on the other hand, various feature elements other than a phase angle are statistically processed to generate an evaluation parameter. Hence, an eddy current testing signal can be judged globally, so that the accuracy of evaluation can be improved. Since the plural feature amounts and evaluation parameters are used, moreover, more accurate evaluation than with the use of a single feature amount and a single evaluation parameter can be made.

17) An apparatus for evaluation of an eddy current testing signal, comprising:

feature amount generation means for generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal highly correlated to a flaw, and an amplitude of the sample eddy current testing signal, but also a feature highly correlated to a secondary factor which affects a waveform of the sample eddy current testing signal;

correct data supply means for supplying known correct answer data as a state signal generated responsive to and representing the flaw or pseudo-factor of the standard specimen;

learning means for receiving the feature amount and the correct answer data, and generating an evaluation parameter by learning with use of the feature amount, the evaluation parameter being a parameter for outputting a value with a sufficiently small error relative to the correct answer data;

evaluation parameter generation means for repeating operations for generation of the feature amount based on the sample eddy current testing signal and generation of the evaluation parameter, while changing a combination of elements of the feature amount, to generate a plurality of evaluation parameters;

feature amount generation means for generating a plurality of feature amounts similar to those from the sample eddy current testing signal for different combinations of elements of the feature amount by use of an actual measurement eddy current testing signal obtained by eddy current testing of a member as an object to be measured;

evaluation results generation means for generating state signals representing a flaw or a pseudo-factor for the respective evaluation parameters on the basis of the respective feature amounts based on the actual measurement eddy current testing signal, and the respective evaluation parameters corresponding to the respective feature amounts; and verification means for comparing the respective state signals which have been obtained as output signals from the evaluation results generation means, and when states represented by the respective state signals are consistent, identifying the states to be a flaw or a pseudo-factor.

According to this aspect, plural feature amounts as numerical expressions of features effective for evaluating whether the state under evaluation is a flaw or other pseudo-factor are statistically processed to generate plural evaluation parameters. The use of such evaluation parameters makes it possible to evaluate whether the state under evaluation is a flaw or other pseudo-factor. Consequently, this aspect of the invention can markedly improve accuracy of evaluation in comparison with judging, based only on the phase angle and amplitude, whether the state under evaluation is a flaw or other pseudo-factor.

In evaluating whether the state under evaluation is a flaw or other pseudo-factor, a person finds it difficult to make evaluation with the concomitant use of a feature element other than a phase angle. According to the above aspect of the invention, on the other hand, various feature elements other than a phase angle are statistically processed to generate an evaluation parameter. Hence, an eddy current testing signal can be judged globally, so that the accuracy of evaluation can be improved. Since the plural feature amounts and evaluation parameters are used, moreover, more accurate evaluation than when using a single feature amount and a single evaluation parameter can be performed.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DESCRIPTION OF THE PREFERRED EMBODIMENTS

Embodiments of the present invention will now be described in detail with reference to the accompanying drawings.

<First Embodiment>

Figure 1:
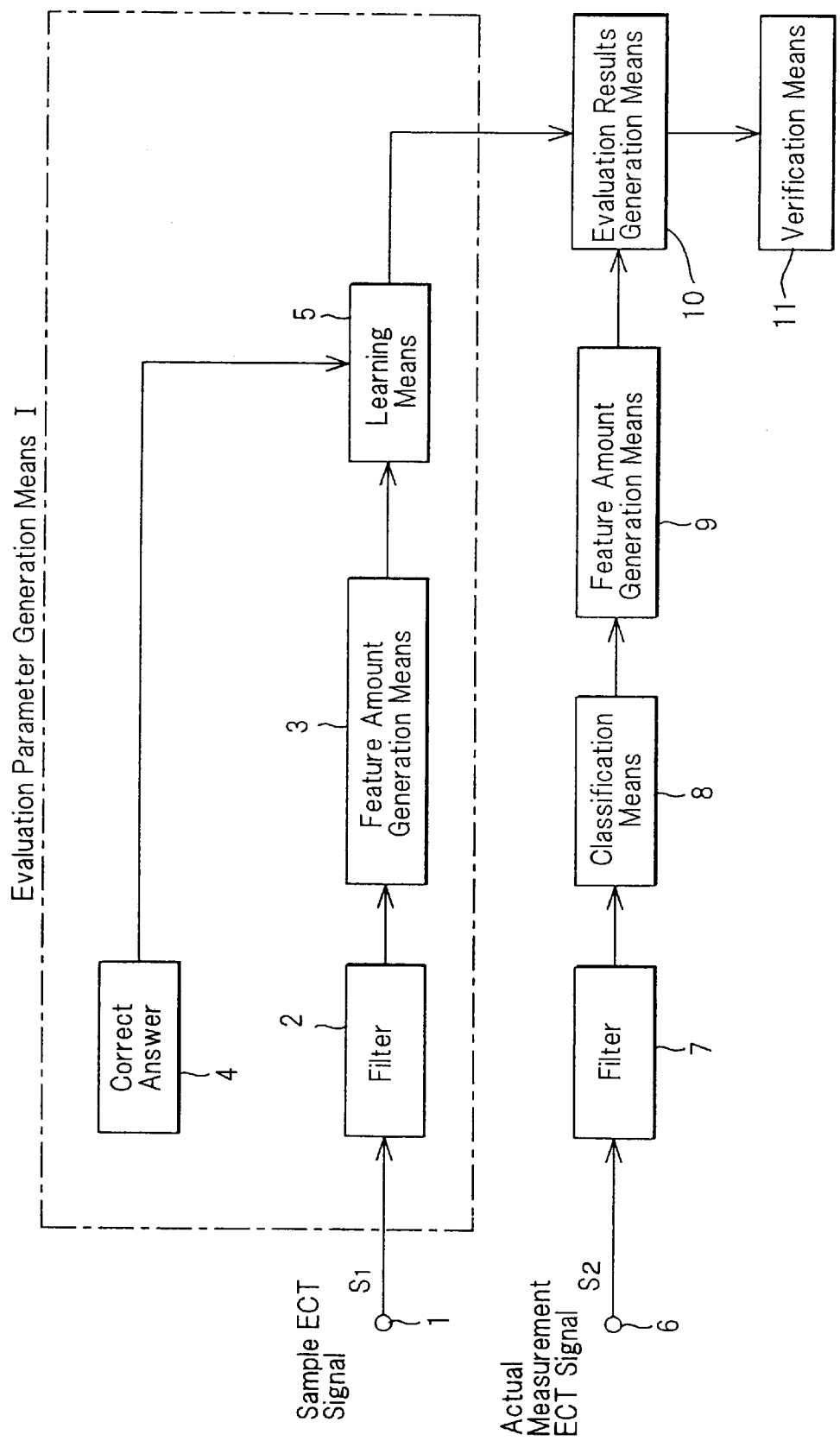
FIG. 1 is a block diagram of an apparatus for evaluation of an eddy current testing signal according to a first embodiment of the present invention.

FIG. 1 is a block diagram of an apparatus for evaluation of an eddy current testing signal according to a first embodiment of the present invention. This embodiment is directed to an apparatus in which an eddy current testing sensor is inserted into a heat exchange tube to perform flaw testing, and the depth of a flaw is evaluated based on an eddy current testing signal obtained by the test. The eddy current testing sensor for obtaining the eddy current testing signal is a multi-coil system type sensor comprising many coils arranged in a circumferential direction in the form of a ring. Based on pitches between the adjacent coils, this sensor can obtain an eddy current testing signal representing the state of an inner peripheral surface of the heat exchange tube. A similar eddy current testing signal can be obtained by an eddy current testing sensor in which a single coil is moved axially while being rotated in the circumferential direction. Needless to say, a member to be measured need not be restricted to a heat exchange tube.

As shown in FIG. 1, an input terminal 1 is supplied with a sample eddy current testing signal $S_1$ obtained by measuring a standard specimen which is a member to be measured and of a known flaw depth. The standard specimen, for example, refers to a member to be measured, in which an internal or external flaw is formed, and its states such as the depth of flaw (e.g., 10%, 20% . . . ; % of total wall thickness) are known. As the sample eddy current testing signal $S_1$, many types of samples corresponding to the states of the flaw are on hand, and supplied sequentially to the input terminal 1.

The sample eddy current testing signal $S_1$ is supplied to feature amount generation means 3 after a noise is reduced by a filter 2 according to a known method, if desired. The feature amount generation means 3 generates a feature amount based on the sample eddy current testing signal $S_1$, the feature amount being a numerical expression of not only the phase angle of the signal highly correlated to the depth of the flaw, and the amplitude of the signal, but also a feature highly correlated to a secondary factor which is other than the depth of the flaw and which affects the waveform of the sample eddy current testing signal $S_1$. Examples of the secondary factor, which is other than the depth of the flaw and which affects the waveform of an eddy current testing signal, are the distribution shape of the eddy current testing signal (length and width of the distribution), the waveform of the eddy current testing signal, a signal waveform near a peak of the amplitude of the eddy current testing signal, and correlation between signals with different exciting frequencies. That is, signals in the neighborhood of the peak of the eddy current testing signal are incorporated into the feature amount to extract an amount contributing to an improvement in the accuracy of the eddy current testing. More concretely, emphasis is placed on a phase angle $\theta_1$ obtained with the use of an exciting current of a certain frequency $f_1$. An amplitude $A_1$ at the frequency $f_1$, a phase angle $\theta_2$ obtained with the use of an exciting current of other frequency $f_2$, an amplitude $A_2$ at the frequency $f_2$, the ratio of amplitudes $(A_1/A_2)$ at frequencies $f_1$ and $f_2$, the width W of the flaw, and the length L of the flaw are used as feature elements in addition to the phase angle $\theta_1$ as the central element. In this manner, a feature amount suitable for attaining the intended purposes can be constituted arbitrarily.

Correct answer data supply means 4 supplies known correct answer data as an amount expressing the depth of the flaw of the standard specimen. The correct answer data are data representing correct answers for the values of the flaw depths based on the sample eddy current testing signal $S_1$ that correspond to the sample eddy current testing signal $S_1$. Learning means 5 receives the feature amount and the correct answer data, and generates an evaluation parameter by learning with use of the feature amount, the evaluation parameter being a parameter for outputting a value with a sufficiently small error relative to the correct answer data. Concretely, the action of the learning means 5 is to perform an operation for determining, by learning, an evaluation parameter, for example, a weighting factor to be applied to the feature amount for outputting a value with a sufficiently small error relative to the amount represented by the correct answer data. The learning method need not be restricted, but may, for example, be a method using a neural network, multiple regression analysis, or the Mahalanobis generalized distance method. That is, this learning means uses various sample eddy current testing signals $S_1$ to obtain evaluation standards from the sample eddy current testing signals $S_1$ statistically.

Evaluation parameter generation means I comprises the filter 2, the feature amount generation means 3, the correct answer data supply means 4, and the learning means 5, as described above. At the evaluation parameter generation means I, operations for generating the feature amounts and the evaluation parameters based on the sample eddy current testing signals $S_1$ are repeated, with the combination of elements of the feature amount being changed, to generate a plurality of evaluation parameters. The combination of elements of the feature amount herein refers to a combination of features, including the aforementioned secondary factor, centered on the phase angle of the sample eddy current testing signal $S_1$, or a combination of features, including the aforementioned secondary factor, centered on the amplitude of the sample eddy current testing signal $S_1$. In short, a suitable combination of the different basic element and other feature is used. In the present embodiment, two types of combinations are available. However, the number of the combinations is not restricted thereto.

Furthermore, the evaluation parameters are generated for each different type of flaws. The types of flaws herein refer to an internal flaw, an external flaw, an axial flaw, and a circumferential flaw. The axial flaw and the circumferential flaw can be discerned based on the phase angle of the eddy current testing signal.

An input terminal 6 is supplied with an actual measurement eddy current testing signal $S_2$ obtained by measuring a member as an object to be measured. The actual measurement eddy current testing signal $S_2$ is supplied to classification means 8 after a noise is reduced by a filter 7 according to a known method, if desired. The classification means 8 discerns the type of a flaw on the basis of the actual measurement eddy current testing signal $S_2$. This is intended to evaluate th e signal by use of evaluation parameters according to the types of flaws, thereby improving accuracy of the evaluation.

Feature amount generation means 9 generates a plurality of feature amounts similar to those from the sample eddy current testing signal $S_1$ for different combinations of elements of the feature amount by use of the actual measurement eddy current testing signal $S_2$. Evaluation results generation means 10 generates data representing the depth of the flaw for the respective evaluation parameters on the basis of the respective feature amounts based on the actual measurement eddy current testing signal $S_2$, and the respective evaluation parameters corresponding to the respective feature amounts. Concretely, the respective feature amounts are processed using the evaluation parameters. For example, data corresponding to the correct answer data are generated by the same processing as that for leading up to the correct answer data based on the sample eddy current testing signal $S_1$, e.g., multiplication of the feature element by the parameter.

Verification means 11 compares the respective data representing the depths of the flaw that have been obtained as output signals from the evaluation results generation means 10. When the depths of the flaw represented by the respective data fall within a predetermined range, the verification means 10 adopts the depth of the flaw based on this range as an estimated value.

Figure 2:
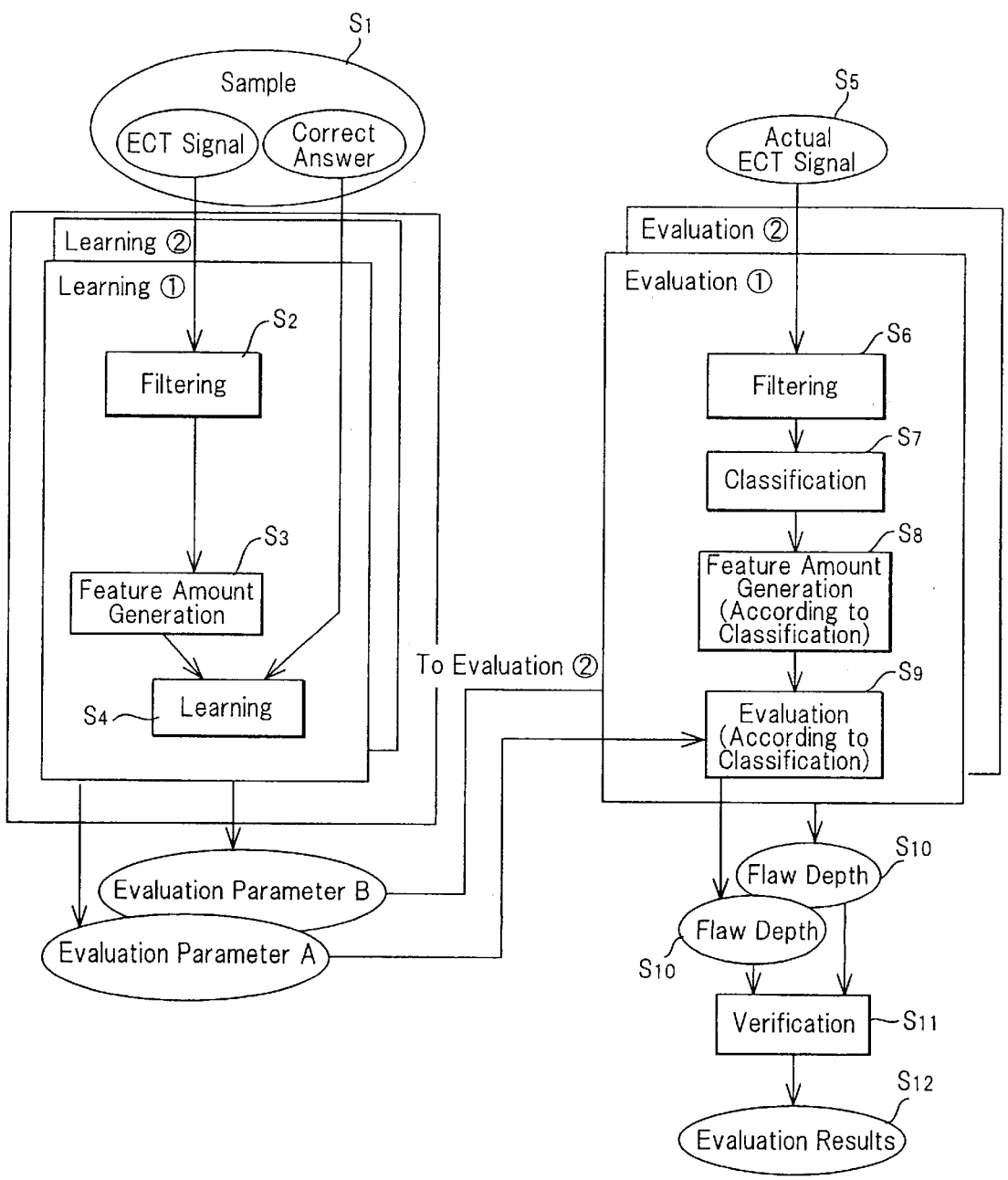
FIG. 2 is an explanation drawing showing a procedure for processing of information in the apparatus of FIG. 1.

An evaluation method using the foregoing apparatus for evaluation of an eddy current testing signal will be described in detail with additional reference to FIG. 2. First, a sample eddy current testing signal $S_1$ is entered (Step S1). After a predetermined filtering treatment (Step S2) is performed, a feature amount is generated (Step S3). Then, correct answer data (Step S1) is referred to, and an evaluation parameter, a parameter for outputting a value with a sufficiently small error relative to the correct answer data, is generated by learning with use of the feature amount (Step S4). As a result, one type of evaluation parameter, A, is generated. The processings of Steps S1 to S4 are repeated to generate another type of evaluation parameter, B. The evaluation parameters A and B are generated for different types of flaws.

Then, an actual measurement eddy current testing signal $S_2$ is entered (Step S5). After a predetermined filtering treatment (Step S6) is performed, the type of a flaw is classified (Step S7). According to this classification, the same feature amount as that from the sample eddy current testing signal $S_1$ is generated (Step S8). Further, data representing the depth of the flaw are generated on the basis of the feature amount based on the actual measurement eddy current testing signal $S_2$, and on the basis of the evaluation parameter A corresponding to the feature amount (Steps A9 and S10). These processings are performed for the evaluation parameter B. Respective data representing the depths of the flaw, which have been obtained by the above processings, are compared for verification (Step S11). When the depths of the flaw represented by the respective data fall within a predetermined range, the depth of the flaw based on this range is adopted as an estimated value (Step S12).

<Second Embodiment>

Figure 3:
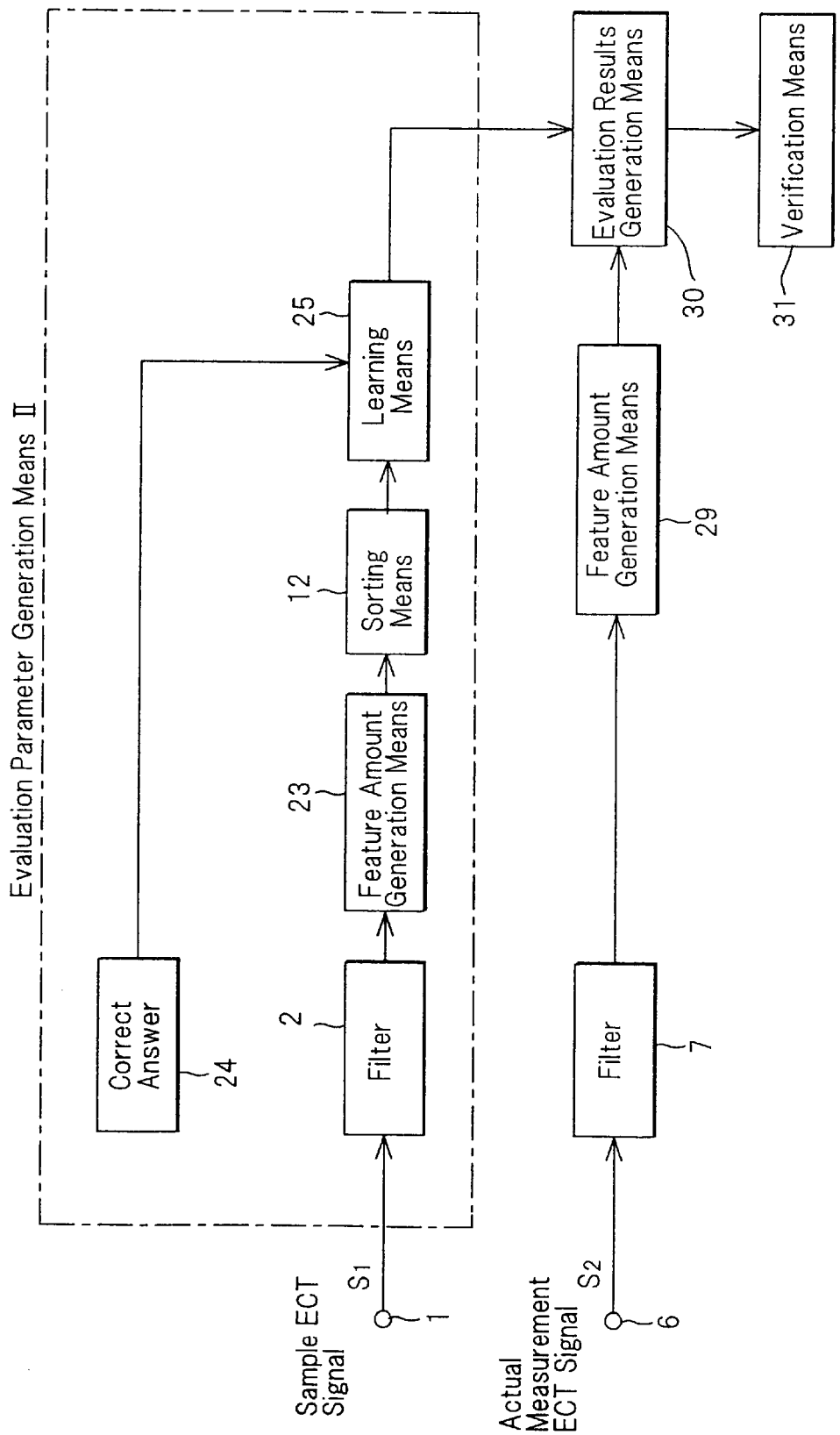
FIG. 3 is a block diagram of an apparatus for evaluation of an eddy current testing signal according to a second embodiment of the present invention.

FIG. 3 is a block diagram of an apparatus for evaluation of an eddy current testing signal according to a second embodiment of the present invention. This embodiment is directed to the evaluation of the amount of a decrease in the wall thickness of a member to be measured, instead of the depth of the flaw evaluated in the First Embodiment. The present apparatus is constituted in the same manner as is the apparatus of the First Embodiment, except that sorting means 12 is added. However, the functions of the respective parts somewhat differ. Thus, the present apparatus will be described mainly concerning the sorting means 12 and the differences from the First Embodiment. The decrease in the wall thickness of the member to be measured is predetected by other method, and an actual measurement eddy current testing signal $S_2$ on this member is obtained. An eddy current testing sensor for obtaining an eddy current testing signal is the same as in the First Embodiment.

As shown in FIG. 3, an input terminal 1 is supplied with a sample eddy current testing signal $S_1$ obtained by measuring a standard specimen as a member to be measured, which has a known amount of decrease in wall thickness. The sample eddy current testing signal $S_1$ is supplied to feature amount generation means 23 after a noise is reduced by a filter 2 according to a known method, if desired. The feature amount generation means 23 generates a feature amount based on the sample eddy current testing signal $S_1$, the feature amount being a numerical expression of not only the phase angle of the signal highly correlated to the amount of decrease in wall thickness, and the amplitude of the signal, but also a feature highly correlated to a secondary factor which is other than the amount of decrease in wall thickness and which affects the waveform of the sample eddy current testing signal $S_1$. Examples of the secondary factor, which is other than the amount of decrease in wall thickness and affects the waveform of the eddy current testing signal, may be the same as those for the depth of the flaw in the First Embodiment. That is, suitably selected feature elements are combined to generate a desired feature amount.

The sorting means 12 exists in the present embodiment. The sorting means 12 performs a processing for sorting the feature amounts based on the respective sample eddy current testing signals $S_1$ according to predetermined standards, such as a sequence of phase, so that an efficiency of subsequent learning is improved. An example of the processing may be a sorting method, such as sorting the feature amounts in order of decreasing magnitude of phase, or in order of decreasing magnitude of amplitude, in the sample eddy current testing signals $S_1$ which are output signals from the respective coils of the multi-coil eddy current testing sensor.

Correct answer data supply means 24 supplies known correct answer data as an amount expressing the amount of decrease in the wall thickness of the standard specimen. Learning means 25 is basically the same as the learning means 5 shown in FIG. 1. That is, the learning means 25 receives the feature amounts and the correct answer data, and generates an evaluation parameter with use of the feature amounts, the evaluation parameter being a parameter for outputting a value with a sufficiently small error relative to the correct answer data.

Evaluation parameter generation means II comprises the filter 2, the feature amount generation means 23, the sorting means 12, the correct answer data supply means 24, and the learning means 25, as described above. At the evaluation parameter generation means II, operations for generating the feature amounts, sorting, and generating the evaluation parameters, based on the sample eddy current testing signals $S_1$, are repeated, with the combination of elements of the feature amount being changed, to generate a plurality of evaluation parameters. The combination of elements of the feature amount herein may be the same as those in the First Embodiment.

Feature amount generation means 29 generates a plurality of feature amounts similar to those from the sample eddy current testing signals $S_1$ for different combinations of feature elements by use of an actual measurement eddy current testing signal $S_2$ obtained by eddy current testing of a member as an object to be measured. Evaluation results generation means 30 generates data representing the amounts of decrease in wall thickness for the respective evaluation parameters on the basis of the respective feature amounts based on the actual measurement eddy current testing signal $S_2$, and the respective evaluation parameters corresponding to the respective feature amounts. Verification means 31 compares the respective data representing the amounts of decrease in wall thickness that have been obtained as output signals from the evaluation results generation means 30. When the amounts of decrease in wall thickness represented by the respective data fall within a predetermined range, the verification means 31 adopts the amount of decrease in wall thickness based on this range as an estimated value.

Figure 4:
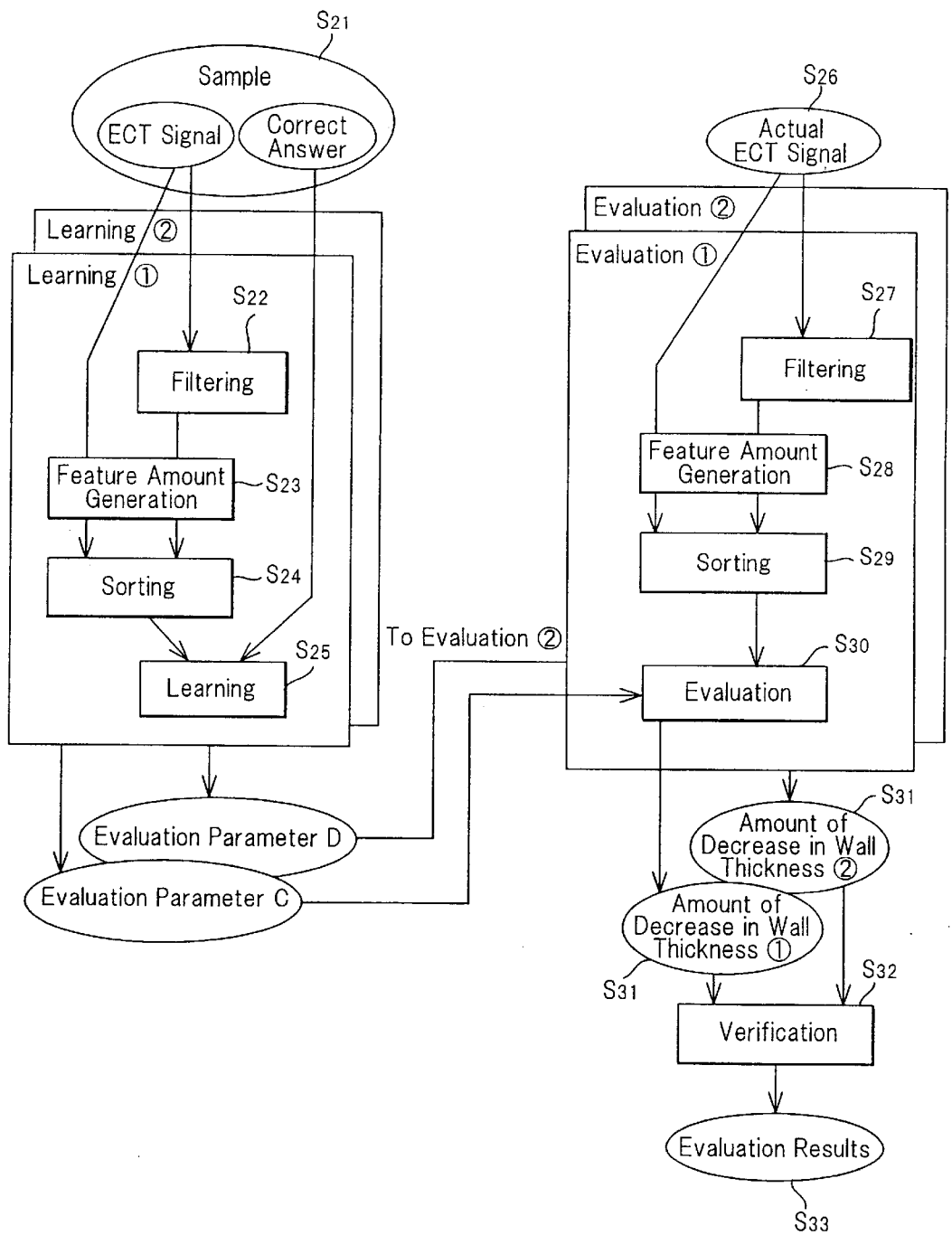
FIG. 4 is an explanation drawing showing a procedure for processing of information in the apparatus of FIG. 3.

An evaluation method using the foregoing apparatus for evaluation of an eddy current testing signal will be described in detail with additional reference to FIG. 4. First, a sample eddy current testing signal $S_1$ is entered (Step S21). After a predetermined filtering treatment (Step S22) is performed, a feature amount is generated (Step S23). Then, feature elements constituting the feature amount are sorted according to predetermined standards (Step S24). Then, correct answer data (Step S21) is referred to, and an evaluation parameter, a parameter for outputting a value with a sufficiently small error relative to the correct answer data, is generated by learning with use of the feature amounts after sorting (Step S25). As a result, one type of evaluation parameter, C, is generated. The processings of Steps S21 to S25 are repeated to generate other type of evaluation parameter, D.

Then, an actual measurement eddy current testing signal $S_2$ is entered (Step S26). After a predetermined filtering treatment (Step S27) is performed, a feature amount similar to that from the sample eddy current testing signal $S_1$ is generated (Step S28), followed by performing predetermined sorting (Step S29). Further, data representing the amounts of decrease in wall thickness are generated on the basis of the feature amount based on the actual measurement eddy current testing signal S2, and on the basis of the evaluation parameter C corresponding to the feature amount (Steps S30 and S31). These processings are performed for the evaluation parameter D. Respective data representing the amounts of decrease in wall thickness, which have been obtained by the above processings, are compared for verification (Step S32). When the amounts of decrease in wall thickness represented by the respective data fall within a predetermined range, the amount of decrease in wall thickness based on this range is adopted as an estimated value (Step S33).

<Third Embodiment>

Figure 5:
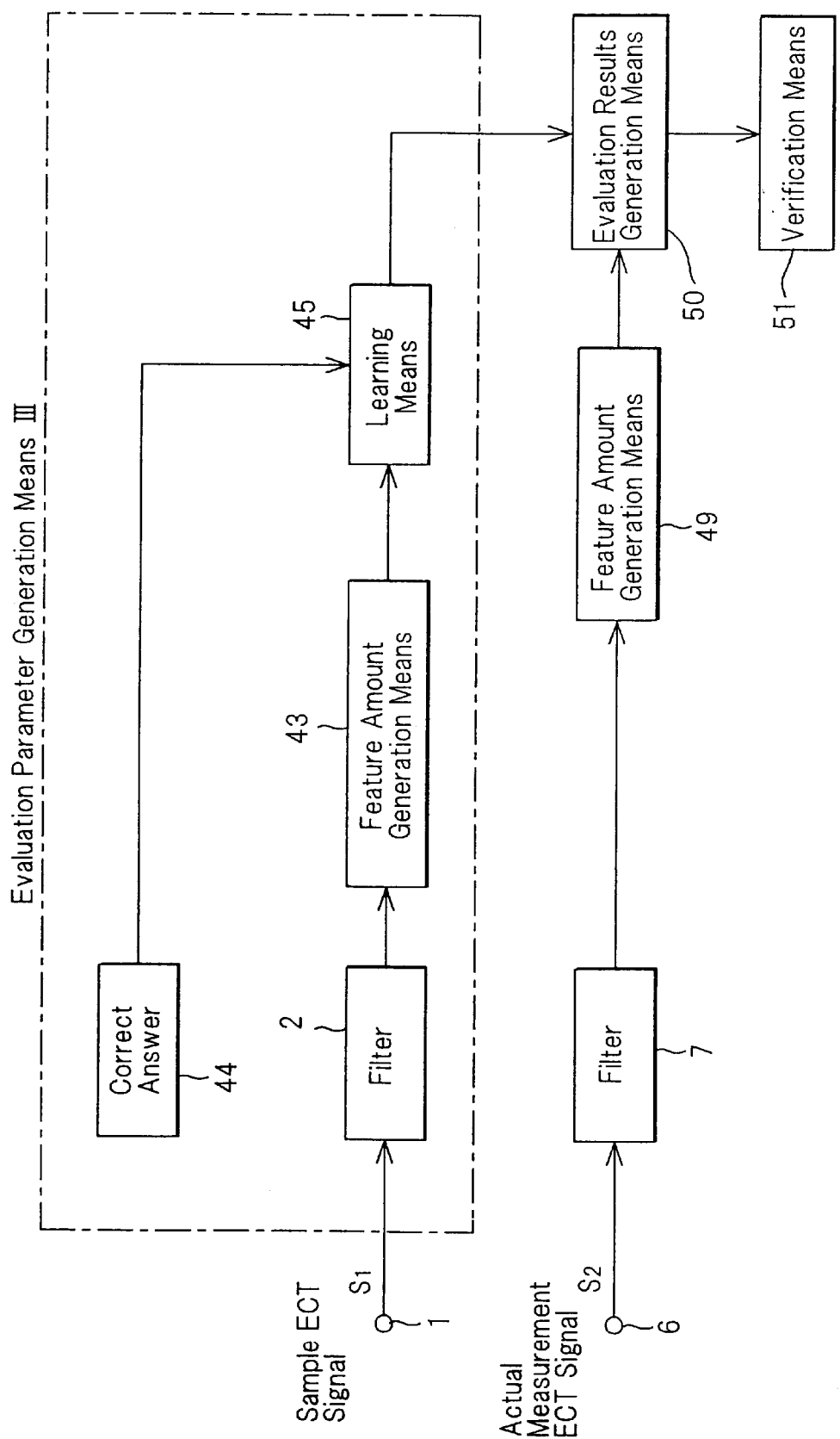
FIG. 5 is a block diagram of an apparatus for evaluation of an eddy current testing signal according to a third embodiment of the present invention.

FIG. 5 is a block diagram of an apparatus for evaluation of an eddy current testing signal according to a third embodiment of the present invention. This embodiment is designed to evaluate whether the eddy current testing signal is ascribed to a flaw of a member to be measured, or is ascribed to a pseudo-factor other than a flaw.

As shown in FIG. 5, an input terminal 1 is supplied with a sample eddy current testing signal $S_1$ obtained by measuring a standard specimen as a member to be measured, which has a known flaw, or a pseudo-factor other than a flaw, as a cause of a false flaw signal. The sample eddy current testing signal $S_1$ is supplied to feature amount generation means 43 after a noise is reduced by a filter 2 according to a known method, if desired. The feature amount generation means 43 generates a feature amount based on the sample eddy current testing signal $S_1$, the feature amount being a numerical expression of not only the phase angle of the signal highly correlated to the flaw, and the amplitude of the signal, but also a feature highly correlated to a secondary factor which is other than a flaw and which affects the waveform of the sample eddy current testing signal $S_1$. Examples of the secondary factor, which is other than a flaw and affects the waveform of an eddy current testing signal, may be the same as those for the depth of the flaw in the First Embodiment. That is, suitably selected feature elements are combined to generate a desired feature amount.

Correct answer data supply means 44 supplies known correct answer data as a state signal generated responsive to and representing the flaw or pseudo-factor of the standard specimen. Learning means 45 is basically the same as the learning means 5 shown in FIG. 1. That is, the learning means 45 receives the feature amounts and the correct answer data, and generates an evaluation parameter with use of the feature amounts, the evaluation parameter being a parameter for outputting a value with a sufficiently small error relative to the correct answer data.

Evaluation parameter generation means III comprises the filter 2, the feature amount generation means 43, the correct answer data supply means 44, and the learning means 45, as described above. At the evaluation parameter generation means III, operations for generating the feature amounts and the evaluation parameters based on the sample eddy current testing signals $S_1$ are repeated, with the combination of elements of the feature amount being changed, to generate a plurality of evaluation parameters. The combination of the feature elements herein may be the same as those in the First Embodiment.

Feature amount generation means 49 generates a plurality of feature amounts similar to those from the sample eddy current testing signals $S_1$ for different combinations of feature elements by use of an actual measurement eddy current testing signal $S_2$ obtained by eddy current testing of a member as an object to be measured. Evaluation results generation means 50 generates state signals representing a flaw or a pseudo-factor for the respective evaluation parameters on the basis of the respective feature amounts based on the actual measurement eddy current testing signal $S_2$, and the respective evaluation parameters corresponding to the respective feature amounts. Verification means 51 compares the respective state signals that have been obtained as output signals from the evaluation results generation means 50. When the states represented by the respective state signals are consistent, the verification means 51 identifies the state as a flaw or a pseudo-factor.

Figure 6:
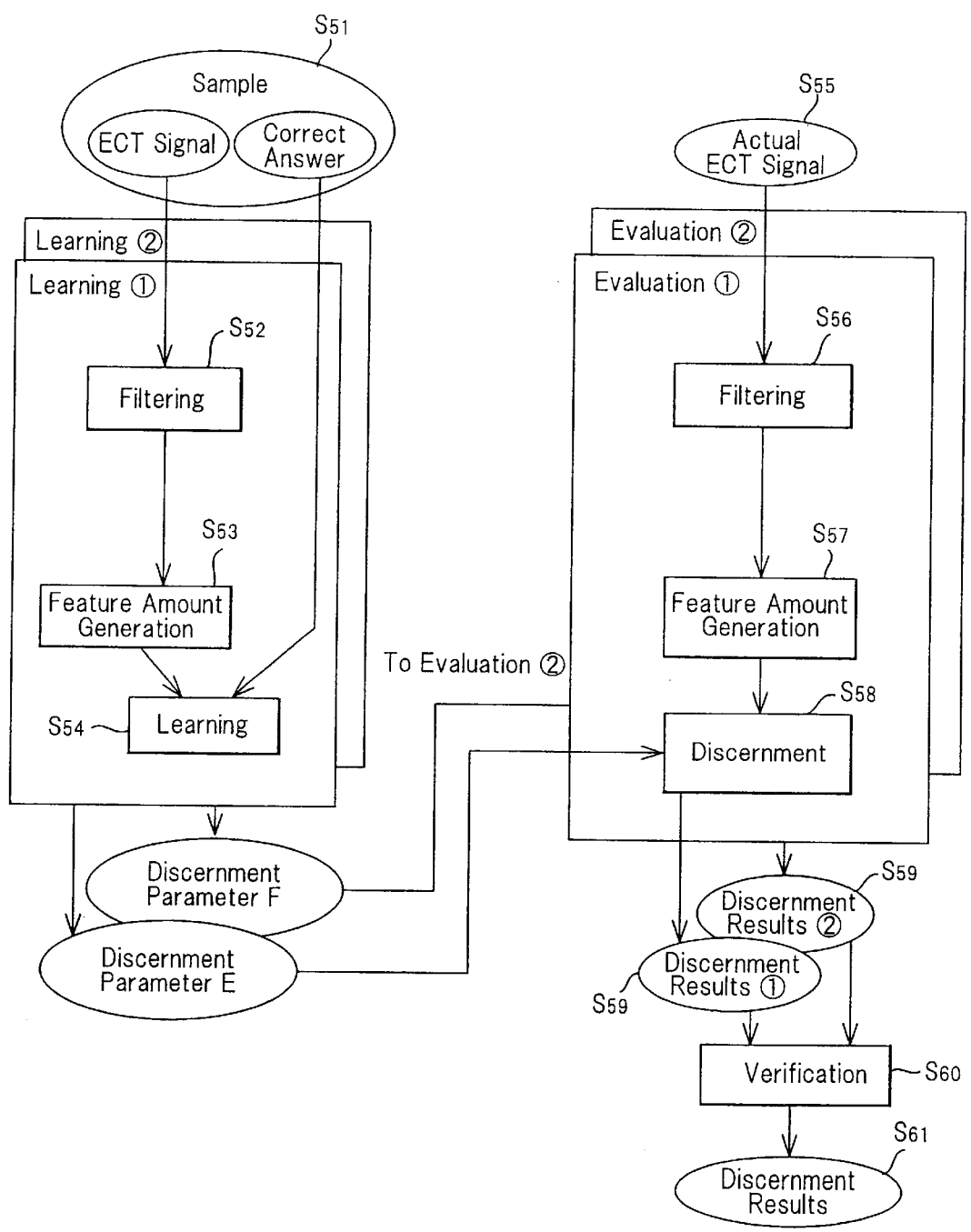
FIG. 6 is an explanation drawing showing a procedure for processing of information in the apparatus of FIG. 5.
Figure 7:
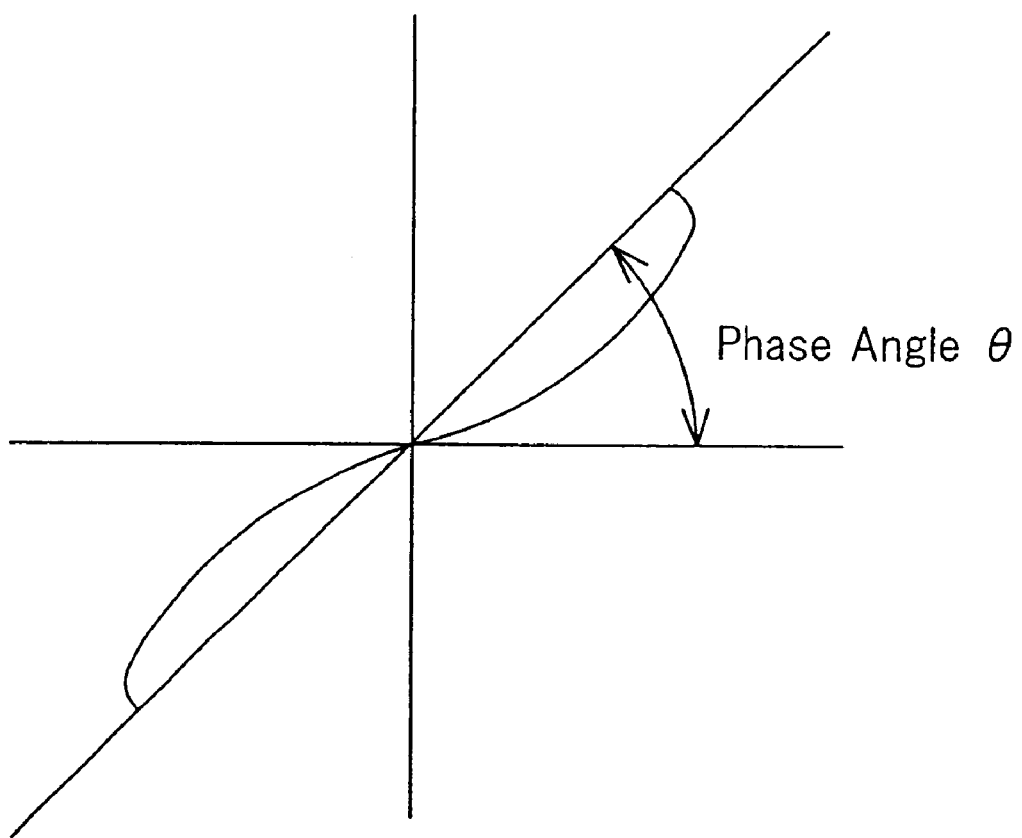
FIG. 7 is a waveform view showing an example of a Lissajous' figure formed on the basis of a flaw when an eddy current testing signal by eddy current testing is expressed on a voltage plane.
Figure 8:
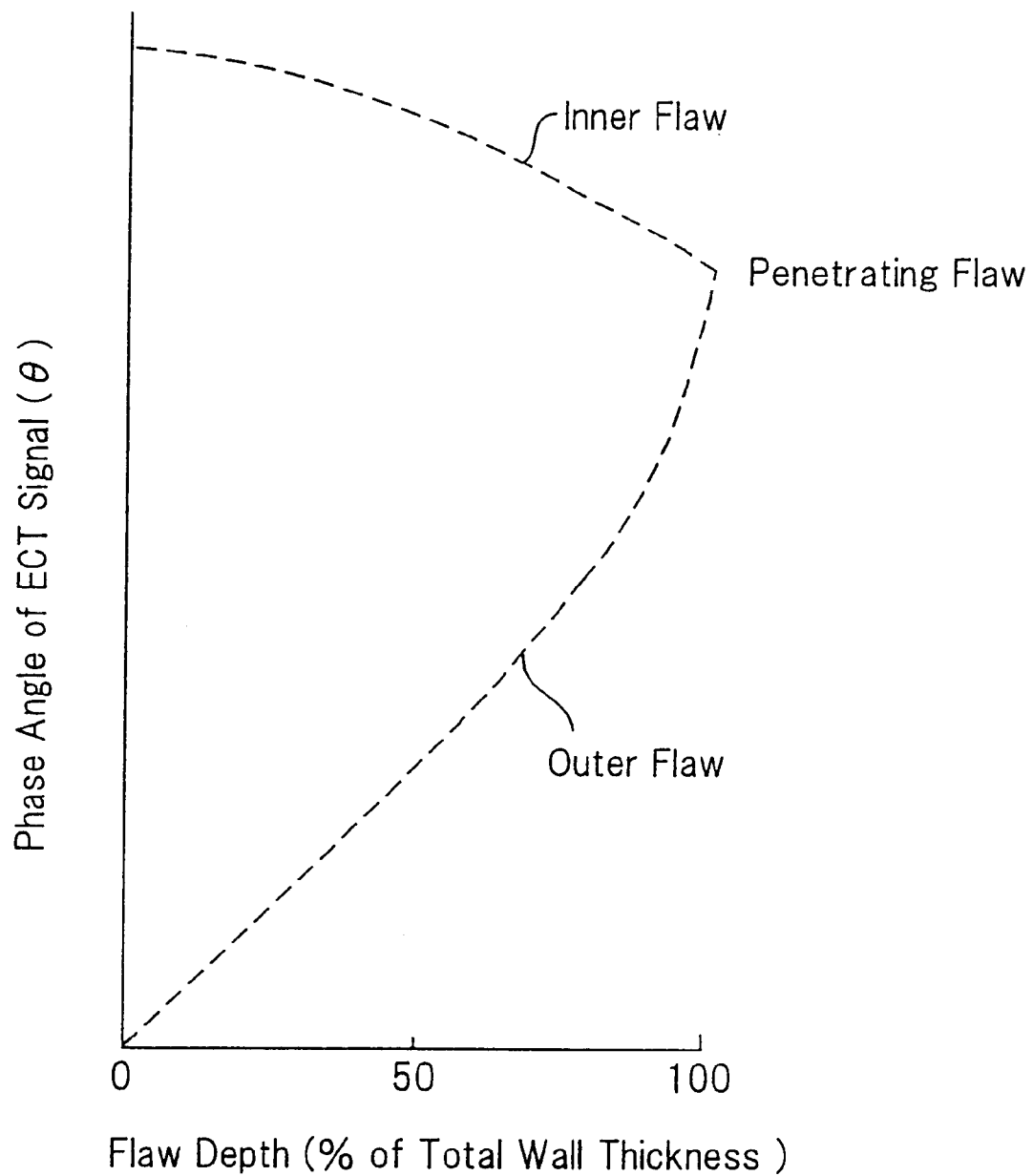
FIG. 8 is a characteristic view showing the relationship between the depth of a flaw and a phase angle used to determine the depth of the flaw based on the waveform view shown in FIG. 7.

An evaluation method using the foregoing apparatus for evaluation of an eddy current testing signal will be described in detail with additional reference to FIG. 6. First, a sample eddy current testing signal $S_1$ is entered (Step S51). After a predetermined filtering treatment (Step S52) is performed, a feature amount is generated (Step S53). Then, correct answer data (Step S51) is referred to, and an evaluation parameter, a parameter for outputting a value with a sufficiently small error relative to the correct answer data, is generated by learning with use of the feature amount (Step S54). As a result, one type of evaluation parameter, E, is generated. The processings of Steps S51 to S54 are repeated to generate other type of evaluation parameter, F. The evaluation parameter E and F are generated according to the types of flaws.

Then, an actual measurement eddy current testing signal $S_2$ is entered (Step S55). After a predetermined filtering treatment (Step S56) is performed, the same feature amount as that from the sample eddy current testing signal $S_1$ is generated (Step S57). Further, a signal representing a flaw or a pseudo-factor is generated on the basis of the feature amount based on the actual measurement eddy current testing signal $S_2$, and on the basis of the evaluation parameter E corresponding to the feature amount (Steps S58 and S59). These processings are performed for the evaluation parameter F. Respective data representing a flaw or other, which have been obtained by the above processings, are compared for verification (Step S60). When the respective data are consistent (i.e. match), the verification results showing a flaw or other are produced (Step S61).

In the First to Third Embodiments, explanations have been provided for two feature amounts and two evaluation parameters. However, these numbers are not restrictive thereto. Of course, the larger their numbers, the higher the accuracy of evaluation. It is not necessarily required to generate them in plural numbers. One type of feature amount, and one type of evaluation parameter are included in the technical concept of the present invention, although they may result in a slightly low accuracy of evaluation. Even in this case, the accuracy of evaluation can be improved markedly compared with earlier technologies.

While the present invention has been described in the foregoing fashion, it is to be understood that the invention is not limited thereby, but may be varied in many other ways. Such variations are not to be regarded as a departure from the spirit and scope of the invention, and all such modifications as would be obvious to one skilled in the art are intended to be included within the scope of the appended claims.

What is claimed is:

1. A method for evaluation of an eddy current testing signal, comprising:

generating a feature amount based on a sample eddy current testing signal obtained by measuring a standard specimen as a member to be measured and of a known depth of a flaw, the feature amount being a numerical expression of not only a phase angle of the sample eddy current testing signal correlated to the depth of the flaw, and an amplitude of the sample eddy current testing signal, but also a feature correlated to a secondary factor which is other than the depth of the flaw and which affects a waveform of the sample eddy current testing signal;

generating an evaluation parameter by learning with use of the feature amount, the evaluation parameter being a parameter for outputting a value with a sufficiently small error relative to known correct answer data as an amount expressing the depth of the flaw of the standard specimen;

generating a feature amount similar to that from the sample eddy current testing signal by use of an actual measurement eddy current testing signal obtained by eddy current testing of a member as an object to be measured; and generating data representing the depth of the flaw on the basis of the feature amount based on the actual measurement eddy current testing signal, and the evaluation parameter corresponding to the feature amount.

2. The method for evaluation of an eddy current testing signal as claimed in claim 1, further comprising:

classifying a type of the flaw, such as an external flaw or an internal flaw, based on the sample eddy current testing signal, and generating a similar feature amount and a similar evaluation parameter according to the classified type; and classifying a type of the flaw based on the actual measurement eddy current testing signal obtained by eddy current testing of the member to be measured, and performing generation of a feature amount according to the classified type, and generation of data representing the depth of the flaw based on the evaluation parameter according to the classified type.

3. A method for evaluation of an eddy current testing signal, comprising:

generating feature amounts based on a plurality of sample eddy current testing signals obtained by measuring a standard specimen, as a member to be measured and with a known amount of decrease in wall thickness, by means of an eddy current testing sensor for obtaining data at a plurality of locations distributed in two-dimensions, such as a multi-coil system sensor having many coils, the feature amounts being numerical expressions of not only phase angles of the sample eddy current testing signals correlated to the amount of decrease in wall thickness, and amplitudes of the sample eddy current testing signals, but also a feature correlated to a secondary factor which is other than the amount of decrease in wall thickness and which affects waveforms of the sample eddy current testing signals;

sorting the feature amounts based on the sample eddy current testing signals according to predetermined standards, such as a sequence of phase;

generating an evaluation parameter by learning with use of the feature amounts, the evaluation parameter being a parameter for outputting a value with a sufficiently small error relative to known correct answer data as an amount expressing the amount of decrease in the wall thickness of the standard specimen;

generating feature amounts similar to those from the sample eddy current testing signals by use of actual measurement eddy current testing signals obtained by eddy current testing of a member to be measured; and generating data representing the amount of decrease in the wall thickness on the basis of the feature amounts based on the actual measurement eddy current testing signals, and the evaluation parameter corresponding to the feature amounts.

4. A method for evaluation of an eddy current testing signal, comprising:

generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal correlated to a flaw, and an amplitude of the sample eddy current testing signal, but also a feature correlated to a secondary factor which affects a waveform of the sample eddy current testing signal;

generating an evaluation parameter by learning with use of the feature amount, the evaluation parameter being a parameter for outputting a value with a sufficiently small error relative to known correct answer data as a state signal representing the flaw or pseudo-factor of the standard specimen;

generating a feature amount similar to that from the sample eddy current testing signal by use of an actual measurement eddy current testing signal obtained by eddy current testing of a member to be measured; and generating a state signal representing the flaw or the pseudo-factor on the basis of the feature amount based on the actual measurement eddy current testing signal, and the evaluation parameter corresponding to the feature amount.

5. An apparatus for evaluation of an eddy current testing signal, comprising:

feature amount generation means for receiving a sample eddy current testing signal obtained by measuring a standard specimen as a member to be measured and of a known depth of a flaw, and generating a feature amount being a numerical expression of not only a phase angle of the sample eddy current testing signal correlated to the depth of the flaw, and an amplitude of the sample eddy current testing signal, but also a feature correlated to a secondary factor which is other than the depth of the flaw and which affects a waveform of the sample eddy current testing signal;

correct answer data supply means for supplying known correct answer data as an amount expressing the depth of the flaw of the standard specimen;

learning means for receiving the feature amount and the correct answer data, and generating an evaluation parameter by learning with use of the feature amount, the evaluation parameter being a parameter for outputting a value with a sufficiently small error relative to the correct answer data;

feature amount generation means for generating a feature amount similar to that from the sample eddy current testing signal by use of an actual measurement eddy current testing signal obtained by eddy current testing of a member as an object to be measured; and evaluation results generation means for generating data representing the depth of the flaw on the basis of the feature amount based on the actual measurement eddy current testing signal, and the evaluation parameter corresponding to the feature amount.

6. The apparatus for evaluation of an eddy current testing signal as claimed in claim 5, further comprising:

classification means for classifying a type of flaw, such as an external flaw or an internal flaw, based on the actual measurement eddy current testing signal obtained by eddy current testing of the member to be measured;

evaluation parameter generation means adapted to classify the type of the flaw based on the sample eddy current testing signal, and generate the feature amount and the evaluation parameter according to the classified type, wherein the feature amount generation means is adapted to generate the feature amount according to a classification made by the classification means, and the evaluation results generation means is adapted to generate the data representing the depth of the flaw on the basis of the feature amount and the evaluation parameter generated according to the classification.

7. An apparatus for evaluation of an eddy current testing signal, comprising:

feature amount generation means for generating feature amounts based on a plurality of sample eddy current testing signals obtained by measuring a standard specimen, as a member to be measured and with a known amount of decrease in wall thickness, by means of an eddy current testing sensor for obtaining data at many locations distributed in two-dimensions, such as a multi-coil system sensor having many coils, the feature amounts being numerical expressions of not only phase angles of the sample eddy current testing signals correlated to the amount of decrease in wall thickness, and amplitudes of the sample eddy current testing signals, but also a feature correlated to a secondary factor which is other than the amount of decrease in wall thickness and which affects waveforms of the sample eddy current testing signals;

sorting means for sorting the feature amounts based on the sample eddy current testing signals according to pre-determined standards, such as a sequence of phase;

correct data supply means for supplying known correct answer data as an amount expressing the amount of decrease in the wall thickness of the standard specimen;

learning means for receiving the feature amounts and the correct answer data, and generating an evaluation parameter by learning with use of the feature amounts, the evaluation parameter being a parameter for outputting a value with a sufficiently small error relative to the correct answer data;

feature amount generation means for generating feature amounts similar to those from the sample eddy current testing signals by use of actual measurement eddy current testing signals obtained by eddy current testing of a member as an object to be measured; and evaluation results generation means for generating data representing an amount of decrease in the wall thickness on the basis of the feature amounts based on the actual measurement eddy current testing signals, and the evaluation parameter corresponding to the feature amounts.

8. An apparatus for evaluation of an eddy current testing signal, comprising:

feature amount generation means for generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal correlated to a flaw, and an amplitude of the sample eddy current testing signal, but also a feature correlated to a secondary factor which affects a waveform of the sample eddy current testing signal;

correct data supply means for supplying known correct answer data as a state signal generated responsive to and expressing the flaw or pseudo-factor of the standard specimen:

learning means for receiving the feature amount and the correct answer data, and generating an evaluation parameter by learning with use of the feature amount, the evaluation parameter being a parameter for outputting a value with a sufficiently small error relative to the correct answer data;

feature amount generation means for generating a feature amount similar to that from the sample eddy current testing signal by use of an actual measurement eddy current testing signal obtained by eddy current testing of a member as an object to be measured; and evaluation results generation means for generating a state signal representing a flaw or a pseudo-factor on the basis of the feature amount based on the actual measurement eddy current testing signal, and the evaluation parameter corresponding to the feature amount.

9. A method for evaluation of an eddy current testing signal, comprising:

generating a feature amount based on a sample eddy current testing signal obtained by measuring a standard specimen as a member to be measured and of a known depth of a flaw, the feature amount being a numerical expression of not only a phase angle of the sample eddy current testing signal correlated to the depth of the flaw, and an amplitude of the sample eddy current testing signal, but also a feature correlated to a secondary factor which is other than the depth of the flaw and which affects a waveform of the sample eddy current testing signal;

generating an evaluation parameter by learning with use of the feature amount, the evaluation parameter being a parameter for leading to known correct answer data as an amount expressing the depth of the flaw of the standard specimen;

repeating operations for generation of the feature amount based on the sample eddy current testing signal and generation of the evaluation parameter, with a combination of elements of the feature amount being changed, to generate a plurality of evaluation parameters;

generating a plurality of feature amounts similar to those from the sample eddy current testing signals for different combinations of elements of the feature amount by use of actual measurement eddy current testing signals obtained by eddy current testing of a member as an object to be measured;

generating data representing the depths of the flaw for the respective evaluation parameters on the basis of the respective feature amounts based on the actual measurement eddy current testing signals, and the respective evaluation parameters corresponding to the respective feature amounts; and comparing the respective data representing the depths of the flaw, and when the depths of the flaw represented by the respective data fall within a predetermined range, adopting the depth of the flaw based on the predetermined range as an estimated value.

10. The method for evaluation of an eddy current testing signal as claimed in claim 9, further comprising:

classifying a type of the flaw, such as an external flaw or an internal flaw, based on the sample eddy current testing signal, and performing similar generation of feature amounts and evaluation parameters according to the classified type; and classifying a type of the flaw based on the actual measurement eddy current testing signal obtained by eddy current testing of the member to be measured, and performing generation of the feature amounts according to the classified type and generation of the data representing the depth of the flaw based on the feature amounts and evaluation parameters according to the classified type.

11. A method for evaluation of an eddy current testing signal, comprising:

generating feature amounts based on a plurality of sample eddy current testing signals obtained by measuring a standard specimen, as a member to be measured and with a known amount of decrease in wall thickness, by means of an eddy current testing sensor for obtaining data at many locations distributed in two-dimensions, such as a multi-coil system sensor having many coils, the feature amounts being numerical expressions of not only phase angles of the sample eddy current testing signals correlated to the amount of decrease in wall thickness, and amplitudes of the sample eddy current testing signals, but also a feature correlated to a secondary factor which is other than the amount of decrease in wall thickness and which affects waveforms of the sample eddy current testing signals;

sorting the feature amounts based on the sample eddy current testing signals according to predetermined standards, such as a sequence of phase;

generating an evaluation parameter by learning with use of the feature amounts, the evaluation parameter being a parameter for outputting a value with a sufficiently small error relative to known correct answer data as an amount expressing the amount of decrease in the wall thickness of the standard specimen;

repeating operations for generation of the feature amounts based on the sample eddy current testing signals, sorting, and generation of the evaluation parameter, while changing a combination of elements of the feature amount and the standards for sorting, to generate a plurality of evaluation parameters;

generating a plurality of feature amounts similar to those from the sample eddy current testing signals for different combinations of elements of the feature amount by use of actual measurement eddy current testing signals obtained by eddy current testing of a member as an object to be measured;

generating data representing the amounts of decrease in the wall thickness for the respective evaluation parameters on the basis of the respective feature amounts based on the actual measurement eddy current testing signals, and the respective evaluation parameters corresponding to the respective feature amounts; and comparing the respective data representing the amounts of decrease in the wall thickness, and when the amounts of decrease in the wall thickness represented by the respective data fall within a predetermined range, adopting the amount of decrease in the wall thickness based on the predetermined range as an estimated value.

12. A method for evaluation of an eddy current testing signal, comprising:

generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal correlated to a flaw, and an amplitude of the sample eddy current testing signal, but also a feature correlated to a secondary factor which affects a waveform of the sample eddy current testing signal;

generating an evaluation parameter by learning with use of the feature amount, the evaluation parameter being a parameter for outputting a value with a sufficiently small error relative to known correct answer data as a state signal representing the flaw or pseudo-factor of the standard specimen;

repeating operations for generation of the feature amount based on the sample eddy current testing signal, and generation of the evaluation parameter, while changing a combination of elements of the feature amount, to generate a plurality of evaluation parameters;

generating a plurality of feature amounts similar to those from the sample eddy current testing signal for different combinations of elements of the feature amount by use of an actual measurement eddy current testing signal obtained by eddy current testing of a member to be measured;

generating state signals representing a flaw or a pseudo-factor for the respective evaluation parameters on the basis of the respective feature amounts based on the actual measurement eddy current testing signal, and the respective evaluation parameters corresponding to the respective feature amounts; and comparing the respective state signals to discern, based on coincidence of contents of the state signals, whether the actual measurement eddy current testing signal is a signal representing a flaw, or a false signal.

13. An apparatus for evaluation of an eddy current testing signal, comprising:

feature amount generation means for receiving a sample eddy current testing signal obtained by measuring a standard specimen as a member to be measured and of a known depth of a flaw, and generating a feature amount being a numerical expression of not only a phase angle of the sample eddy current testing signal correlated to the depth of the flaw, and an amplitude of the sample eddy current testing signal, but also a feature correlated to a secondary factor which is other than the depth of the flaw and which affects a waveform of the sample eddy current testing signal;

correct answer data supply means for supplying known correct answer data as an amount expressing the depth of the flaw of the standard specimen;

learning means for receiving the feature amount and the correct answer data, and generating an evaluation parameter by learning with use of the feature amount, the evaluation parameter being a parameter for outputting a value with a sufficiently small error relative to the correct answer data;

evaluation parameter generation means for repeating operations for generation of the feature amount based on the sample eddy current testing signal and generation of the evaluation parameter, with a combination of elements of the feature amount being changed, to generate a plurality of evaluation parameters;

feature amount generation means for generating a plurality of feature amounts similar to those from the sample eddy current testing signal for different combinations of elements of the feature amount by use of an actual measurement eddy current testing signal obtained by eddy current testing of a member as an object to be measured;

evaluation results generation means for generating data representing depths of a flaw for the respective evaluation parameters on the basis of the respective feature amounts based on the actual measurement eddy current testing signal, and the respective evaluation parameters corresponding to the respective feature amounts; and verification means for comparing the respective data representing the depths of the flaw which have been obtained as output signals from the evaluation results generation means, and when the depths of the flaw represented by the respective data fall within a predetermined range, adopting the depth of the flaw based on the predetermined range as an estimated value.

14. The apparatus for evaluation of an eddy current testing signal as claimed in claim 13, further comprising:

classification means for classifying a type of flaw, such as an external flaw or an internal flaw, based on the actual measurement eddy current testing signal obtained by eddy current testing of the member to be measured, wherein the evaluation parameter generation means is adapted to classify the type of the flaw based on the sample eddy current testing signal, and generate the feature amount and the evaluation parameter according to the classified type, the feature amount generation means is adapted to generate the feature amount according to a classification made by the classification means, and the evaluation results generation means is adapted to generate the data representing the depth of the flaw on the basis of the feature amount and the evaluation parameter generated according to the classification.

15. An apparatus for evaluation of an eddy current testing signal, comprising:

feature amount generation means for generating feature amounts based on a plurality of sample eddy current testing signals obtained by measuring a standard specimen, as a member to be measured and with a known amount of decrease in wall thickness, by means of an eddy current testing sensor for obtaining data at many locations distributed in two-dimensions, such as a multi-coil system sensor having many coils, the feature amounts being numerical expressions of not only phase angles of the sample eddy current testing signals correlated to the amount of decrease in wall thickness, and amplitudes of the sample eddy current testing signals, but also a feature correlated to a secondary factor which is other than the amount of decrease in wall thickness and which affects waveforms of the sample eddy current testing signals;

sorting means for sorting the feature amounts based on the sample eddy current testing signals according to predetermined standards, such as a sequence of phase;

correct data supply means for supplying known correct answer data as an amount expressing the amount of decrease in the wall thickness of the standard specimen;

learning means for receiving the feature amounts and the correct answer data, and generating an evaluation parameter by learning with use of the feature amounts, the evaluation parameter being a parameter for outputting a value with a sufficiently small error relative to the correct answer data;

evaluation parameter generation means for repeating operations for generation of the feature amounts based on the sample eddy current testing signals, sorting, and generation of the evaluation parameter, while changing a combination of elements of the feature amount and the standards for sorting, to generate a plurality of evaluation parameters;

feature amount generation means for generating a plurality of feature amounts similar to those from the sample eddy current testing signals for different combinations of elements of the feature amount by use of actual measurement eddy current testing signals obtained by eddy current testing of a member as an object to be measured;

evaluation results generation means for generating data representing the amounts of decrease in the wall thickness for the respective evaluation parameters on the basis of the respective feature amounts based on the actual measurement eddy current testing signals, and the respective evaluation parameters corresponding to the respective feature amounts; and verification means for comparing the respective data representing the amounts of decrease in the wall thickness which have been obtained as output signals from the evaluation results generation means, and when the amounts of decrease in the wall thickness represented by the respective data fall within a predetermined range, adopting the amount of decrease in the wall thickness based on the predetermined range as an estimated value.

16. An apparatus for evaluation of an eddy current testing signal, comprising:

feature amount generation means for generating a feature amount based on a sample eddy current testing signal obtained by measuring a standard specimen as a member to be measured, which has a known flaw or has formed a pseudo-factor other than a flaw as a cause of a false eddy current testing signal, the feature amount being a numerical expression of not only a phase angle of the sample eddy current testing signal correlated to a flaw, and an amplitude of the sample eddy current testing signal, but also a feature correlated to a secondary factor which affects a waveform of the sample eddy current testing signal;

correct data supply means for supplying known correct answer data as a state signal generated responsive to and representing the flaw or pseudo-factor of the standard specimen;

learning means for receiving the feature amount and the correct answer data, and generating an evaluation parameter by learning with use of the feature amount, the evaluation parameter being a parameter for outputting a value with a sufficiently small error relative to the correct answer data;

evaluation parameter generation means for repeating operations for generation of the feature amount based on the sample eddy current testing signal and generation of the evaluation parameter, while changing a combination of elements of the feature amount, to generate a plurality of evaluation parameters;

feature amount generation means for generating a plurality of feature amounts similar to those from the sample eddy current testing signal for different combinations of elements of the feature amount by use of an actual measurement eddy current testing signal obtained by eddy current testing of a member as an object to be measured;

evaluation results generation means for generating state signals representing a flaw or a pseudo-factor for the respective evaluation parameters on the basis of the respective feature amounts based on the actual measurement eddy current testing signal, and the respective evaluation parameters corresponding to the respective feature amounts; and verification means for comparing the respective state signals which have been obtained as output signals from the evaluation results generation means, and when states represented by the respective state signals are consistent, identifying the states to be a flaw or a pseudo-factor.

* * * * *